United States Patent [19]

Casper

[11] Patent Number: 5,422,119

[45] Date of Patent: * Jun. 6, 1995

[54] TRANSDERMAL HORMONE REPLACEMENT THERAPY

[75] Inventor: Robert F. Casper, Toronto, Canada

[73] Assignee: Jencap Research Ltd., Toronto, Canada

[*] Notice: The portion of the term of this patent subsequent to Apr. 28, 2009 has been disclaimed.

[21] Appl. No.: 177,355

[22] Filed: Jan. 3, 1994

Related U.S. Application Data

[60] Continuation-in-part of Ser. No. 996,820, Dec. 28, 1992, abandoned, which is a continuation-in-part of Ser. No. 974,182, Nov. 10, 1992, Pat. No. 5,256,421, which is a division of Ser. No. 874,016, Apr. 27, 1992, abandoned, which is a continuation of Ser. No. 515,691, Apr. 26, 1990, Pat. No. 5,108,995, which is a continuation of Ser. No. 247,861, Sep. 22, 1988, abandoned.

[30] Foreign Application Priority Data

Sep. 24, 1987 [CA] Canada ................................ 547743
Sep. 24, 1987 [CA] Canada ................................ 547943

[51] Int. Cl.⁶ .................. A61K 31/565; A61K 31/57; A61K 31/58; A61L 15/03
[52] U.S. Cl. ..................................... 424/449; 514/170
[58] Field of Search .......................... 424/449; 514/170

[56] References Cited

U.S. PATENT DOCUMENTS 5,108,995  4/1992  Casper ................................ 514/170
5,256,421  10/1993  Casper ................................ 424/449

*Primary Examiner*—Shep K. Rose
*Attorney, Agent, or Firm*—Evenson, McKeown, Edwards & Lenahan

[57] ABSTRACT

The present invention provides a method of treating a female in need of hormone replacement therapy comprising transdermally administering to said female a series of alternating phases of from about one to about four days of estrogen dominant activity and phases of from about one to about four days of progestin dominant activity, with the estrogen dominant activity phase consisting of administering a transdermal estrogen substance alone or administering a transdermal estrogen substance and a transdermal progestin substance and the progestin dominant activity phase consisting of administering a transdermal progestin substance and a transdermal estrogen substance, the amount of progestin substance being alternately increased in the progestin dominant activity phase and decreased in the estrogen dominant activity phase to provide the required dominant activity.

39 Claims, No Drawings

TRANSDERMAL HORMONE REPLACEMENT THERAPY

CROSS-REFERENCES TO RELATED APPLICATIONS

This application is a continuation-in-part of my application Ser. No. 07/996,820, filed Dec. 28, 1992 (now abandoned), which in turn is a continuation-in-part of U.S. application Ser. No. 07/974,182, filed Nov. 10, 1992 (now U.S. Pat. No. 5,256,421), which is a division of application Ser. No. 07/874,016, filed Apr. 27, 1992 (now abandoned), which in turn was a continuation of application Ser. No. 07/515,691, filed Apr. 26, 1990, (now U.S. Pat. No. 5,108,995), which in turn was a continuation of application Ser. No. 07/247,861, filed Sep. 22, 1988.

FIELD OF THE INVENTION

This invention relates to hormone replacement therapy for menopausal or castrate women. In particular, this invention relates to a form of a preparation and method which involves transdermal delivery.

DESCRIPTION OF THE RELATED ART

Estrogen replacement therapy is warranted in menopausal women for several reasons. Estrogen :replacement is known to relieve hot flushes and this relief of flushes and night sweats improves sleep patterns and contributes to the patient's general feeling of well-being. Estrogen replacement protects against postmenopausal loss of calcium from the skeleton, especially from vertebral bodies, preventing crush fractures and loss of body height. Several studies have now reported that long-term estrogen therapy is also associated with a reduction in the incidence of classical osteoporotic fractures of the forearm and hip. Another beneficial effect of long-term estrogen use is the reduction of the risk of death from ischemic heart disease probably mediated by changes in blood lipoprotein concentrations. Estrogen replacement has also been shown to improve the vascularity and health of the vaginal mucosa and urinary tract. The only major risk factor associated with estrogen administration in the doses required to relieve menopausal symptoms, is hyperstimulation of the endometrium and an increased risk of endometrial cancer. The addition of a progestin for 13 days each month has been demonstrated to protect the endometrium from these stimulatory effects of estrogen.

Progestin protects the endometrium by reducing nuclear estradiol receptor concentration and thereby decreasing nuclear estrogen bioavailability resulting in an antimitotic effect and lowering DNA synthesis. Progestins also increase the activity of endometrial estradiol-$17\beta$-dehydrogenase, an enzyme which metabolizes estradiol to estrone, a less potent estrogen. However, concerns have been expressed about the potential adverse effects of progestin in suppressing high density lipoprotein cholesterol concentrations. This cholesterol fraction appears to have a protective effect against ischemic heart disease and atherosclerosis. The lowering of HDL cholesterol by progestin could negate the long-term beneficial effects of estrogen in reducing the incidence of myocardial infraction. Other side effects of progestins include acne, breast tenderness, depression and irritability. Since the side effects of progestins appear to be dose dependent, the dose of progestin used with postmenopausal estrogen replacement should be the minimum necessary to achieve endometrial protection.

Current hormonal replacement consists of continuous (daily or cyclic) (example days 1-25 of each month) estrogen administration with the addition of a progestin for 10-13 days each month (example days 13-25 of each month). This type of replacement regimen is effective in preventing menopausal symptoms and at the same time, protects the endometrium against the development of hyperplasia or adenocarcinoma. However, the cyclic administration of a progestin leads to a scheduled withdrawal bleed or period in 65-75% of women. This withdrawal bleeding is usually not welcomed by the patient and can lead to problems with compliance. Also because the progestin administration is preceded by up to 13-16 days of unopposed estrogen therapy with endometrial proliferation and estrogen and progestin receptor induction, it is possible that a high dose of progestin is required to antagonize these effects resulting in a greater chance of side effects and adverse metabolic effects. While newer continuous low dose estrogen and progestin regimens for hormonal replacement may avoid the problem of withdrawal bleeding, daily administration of a progestin in these regimens induces depletion of both estrogen and progestin receptors resulting in endometrial atrophy which may be associated with breakthrough bleeding. Since abnormal bleeding in a postmenopausal woman is known to be associated with endometrial carcinoma, it must be investigated by endometrial sampling for hypertrophy usually by D&C. Daily administration of a progestin also raises the concern that the favorable effects of estrogen on HDL cholesterol metabolism will be adversely affected with a fall in HDL cholesterol.

Thus, in U.S. Pat. No. 5,108,995 the present applicant has described a regimen which is better able to protect the endometrium against the estrogen related risk of endometrial hyperplasia and adenocarcinoma with a lower dose of progestin by administering progestin for a short period of time alternating with a short period of absent or reduced progestin. The formulation administers a low dose of progestin intermittently throughout the month, and as a result the following are achieved: the substantial elimination of withdrawal bleeding; intermittent increases in estrogen activity; and stimulation of endometrial growth and progestin receptors. Consequently the endometrium is more sensitive to subsequent progestin activity which limits growth by decreasing estrogen receptors and increasing $17\beta$-hydroxysteroid dehydrogenase. Interaction of progestin with progestin receptors induces secretory changes in the endometrium which results in a denser stroma and endometrial stability. A return to relatively dominant estrogenic activity then again stimulates estrogen and progestin receptors and renews endometrial sensitivity to progestin. This push/pull activity keeps endometrial activity within a low range depending on the number of days of estrogenic and progestagenic activity and maintains a stable endometrium resulting in the substantial absence of breakthrough or withdrawal bleeding. This formulation allows better progestational effects with less progestin. The dose of progestin is significantly decreased compared with a preparation containing a constant daily dosage of a progestin. A total steroid dosage can be achieved which is similar to or even lower than that of the present cyclic method of administering estrogen and progestin for hormonal replacement therapy of ovarian failure. A reduction in progestin dosage results in less negative impact on HDL cholesterol levels.

Transdermal drug delivery systems are known in the art. Some patents in this area are concerned with the transdermal delivery of hormone formulations for various purposes. Examples of such patents are as follows:

U.S. Pat. No. 4,816,258 issued Mar. 28, 1989 to Nedberge et al discloses a drug formulation of ethinyl estradiol and levo-norgestrel for transdermal administration which comprises a matrix containing the steroids and a skin permeation enhancing amount of glycerol monooleate.

U.S. Pat. No. 5,122,382 issued Jun. 16, 1992 to Gail et al discloses a composition for transdermal administration comprising an estrogen and ST-1435. The formulation delivers certain quantities per day of the steroids and includes a skin permeation enhancer.

U.S. Pat. No. 5,023,084 issued Jun. 11, 1991 and U.S. Pat. No. 4,906,169 issued Mar. 6, 1992, both to Chien et al describe a combination of estrogen and progestin in a contraceptive formulation with a transdermal unit comprising a backing layer, a polymer layer containing the hormones and an adhesive layer.

U.S. Pat. Nos. 4,624,665, issued Nov. 25, 1986, 4,687,481 issued Aug. 18, 1987, 4,834,978 issued May 30, 1989, 4,810,499 issued Mar. 7, 1989 and 4,927,687 issued May 22, 1990 describe a transdermal delivery system which is said to prevent dose dumping of the drug to be delivered caused by accidental rupture of a retaining member and ensures effective and prolonged delivery of the drug, particularly contraceptive steroids. Suitable steroids include norethindrone, norgestrel, estradiol, levo-norgestrel and mestranol.

SUMMARY OF THE INVENTION

The benefits of transdermal delivery systems are perceived to exist primarily in the ability to bypass the liver on the "first pass" of the hormones through the body, by not delivering them orally. Gastrointestinal absorption requires transit through the liver, and metabolism of the drug occurs there, before the first complete circulatory loop, takes the drug to the target organs (i.e., uterus, heart, bones, central nervous system, etc.). The advantage of avoiding the liver is that lower amounts of the drug can be given to a patient in order to achieve the same degree of efficacy in target tissues, thereby diminishing the untoward metabolic effects (e.g., changes in coagulation factors, glucose metabolism, lipids, etc.) that would be encountered via the oral route. (See Transdermal Hormone Replacement, M. I. Whitehead and L. Schenkel, 1990.) It is also thought that avoidance of the stomach could prevent some of the nausea and gastrointestinal distress that is associated with estrogen therapy when taken orally. (See Transdermal Administration of Oestrogen/Progestin Hormone Replacement Therapy, M. I. Whitehead et al, The Lancet, 310–3 12, Feb. 10, 1990.)

It is believed that a continuous transdermal delivery system generally provides more constant steady-state plasma levels of hormones, devoid of peaks and valleys, than does a once daily oral administration. The "first pass" phenomenon could also be argued to underlie the perceived disadvantage of the transdermal delivery route. This perceived disadvantage is that estrogens actually induce some favorable changes in the lipoprotein profile (stimulating increases in HDL cholesterol, for example) and these effects are likely the result of induction of liver enzymes. Diminishing hepatic exposure to the drug could be predicted to diminish the beneficial effects of these drugs.

Nevertheless, there are a number of factors to be weighed in determining whether a patient should be treated with hormone therapy orally versus transdermally, and generally, the factors in favor of transdermal include a patient who is very sensitive to pharmacological agents in general, a noncompliant or forgetful patient who may have difficulty with daily dosing regimens, gastrointestinal disturbances from oral estrogen therapy and a lack of response to the oral route. In contrast, the selection of the oral form might be preferable in the case where a patient is perceived to have a high risk for cardiovascular disease, hyperlipidemia, a tendency to dermal sensitivity and dermatological disorders.

It is believed that the use of a transdermal delivery system for the regimen of U.S. Pat. No. 5,108,995 would enhance the benefits of the basic regimen on its own because of the perceived advantages of the transdermal route. In addition, it has also been found that the transdermal delivery system works best with a particular selection of hormones which are most suitable for this delivery route.

In one form, the invention provides a method of treating a female in need of hormone replacement therapy comprising transdermally administering to said female a pharmaceutical patch regimen series consisting essentially of a series of transdermal patches arranged in alternating phases of dominant hormone activity of from about one day to about four days, said phases being selected from estrogen dominant activity phases and progestin dominant activity phases, each of said phases comprising at least one patch which is applied and removed in accordance with the particular dominant phase activity, wherein the estrogen dominant activity phase contains an amount of a substance exhibiting estrogen activity sufficient to promote the development of progestin receptors in the endometrium of said female, or an amount of a substance exhibiting estrogen activity sufficient to promote the development of progestin receptors in the endometrium of said female and an amount of a substance exhibiting progestin activity; and wherein the progestin dominant activity phases contain an amount of a substance exhibiting estrogen activity and an amount of a substance exhibiting progestin activity sufficient to antagonize the effect of estrogen on the endometrium of said female, and the estrogen and progestin are selected from transdermally administrable hormones.

The present invention provides a method of treating a female in need of hormone replacement therapy comprising transdermally administering to said female a pharmaceutical patch regimen series consisting essentially of a series of transdermal patches arranged in alternating phases of dominant hormone activity of from about one day to about four days, said phases being selected from estrogen dominant activity phases and progestin dominant activity phases, each of said phases comprising at least one patch which is applied and removed in accordance with the particular dominant phase activity, said estrogen dominant activity phase consisting of administering a transdermal estrogen substance alone or administering a transdermal estrogen substance and a transdermal progestin substance, and said progestin dominant activity phase consisting of administering a transdermal progestin substance and a transdermal estrogen substance, the amount of progestin substance being alternately increased in the progestin dominant activity phase and decreased in the estrogen dominant activity phase to provide the required dominant activity.

In another aspect the invention provides a pharmaceutical preparation for administration to a female in need of hormone replacement therapy comprising a patch regimen series consisting essentially of a series of transdermal patches arranged in alternating phases of dominant hormone activity of from about one day to about four days, each of said phases being selected from estrogen dominant activity phases and progestin dominant activity phases, each of said phases comprising at least one patch which is applied and removed in accordance with the particular dominant phase activity, said estrogen dominant activity phase consisting of a transdermal estrogen substance alone or a transdermal estrogen substance and a transdermal progestin substance, and said progestin dominant activity phase consisting of a transdermal progestin substance and a transdermal estrogen substance, the amount of progestin substance being alternately increased in the progestin dominant activity phase and decreased in the estrogen dominant activity phase to provide the required dominant activity.

In another form the invention provides a package comprising a pharmaceutical transdermal patch regimen for administration to a female in need of hormone replacement therapy wherein the package consists of a pharmaceutical patch regimen series consisting essentially of a series of transdermal patches arranged in alternating phases of dominant hormone activity of from about one day to about four days, each of said phases being selected from estrogen dominant activity phases and progestin dominant activity phases, each of said phases comprising at least one patch which is applied and removed in accordance with the particular dominant phase activity, said estrogen dominant activity phase consisting of a transdermal estrogen substance alone or a transdermal estrogen substance and a transdermal progestin substance, and said progestin dominant activity phase consisting of a transdermal progestin substance and a transdermal estrogen substance, the amount of progestin substance being alternately increased in the progestin dominant activity phase and decreased in the estrogen dominant activity phase to provide the required dominant activity.

In a preferred form of the invention the estrogen and progestin are selected from transdermal estrogens and progestins which provide levels of activity, equivalent to a transdermal delivery rate of from about 25 μg/day to about 150 μg/day, more preferably about 100 μg/day of 17-β estradiol and from about 250 μg/day, more preferably about 25 μg/day to about 1000 μg/day of norethindrone acetate or from about 5 μg/day to about 150 μg/day of 3-keto-desogestrel, with the proviso that the progestin is increased in the progestin dominant phase relative to the estrogen dominant phase to produce the required dominance.

In a preferred form of the present invention, a first patch, for example either an adhesive matrix type or a drug reservoir type (ethanolic gel) is prepared containing sufficient 17-β estradiol to provide a transdermal delivery rate of from about 25 μg/day to about 100 μg/day. A second patch is prepared, either adhesive matrix or drug reservoir (ethanolic gel) type containing sufficient 17-β estradiol to give the above release rate and sufficient norethindrone acetate (NETA) to provide a transdermal delivery rate of from about 25 μg/day to about 1000 μg/day of NETA, more preferably from about 75 μg/day to about 500 μg/day, most preferably 75 μg/day to about 300 μg/day. In the case of the combination of 17-β estradiol and 3-ketodesogestrel, the amount of 17-β estradiol remains the same as set out above, while the amount of 3-ketodesogestrel is sufficient to provide a transdermal delivery rate of from about 5 μg/day to about 150 μg/day, more preferably 25 μg/day to about 150 μg/day. It is the application of these patches in the required sequence which provides the advantage of the present invention.

The estrogens which may be employed as a component in the regimens of this invention may be any of those conventionally available which can be absorbed through the skin. Typically, the estrogen may be selected from the group comprising synthetic and natural estrogens. The synthetic estrogens may be selected from, for example, ethinyl estradiol, micronized estradiol, 17β estradiol, mestranol, estradiol valerate, 11-nitrato estradiol, 7-α-methyl-11-nitrato-estradiol, piperazine estrone sulfate and quinestranol. Of particular interest are 17α-ethinylestradiol and esters and ethers thereof. The preferred estrogen is 17-β estradiol.

The progestin component may be any progestationally active compound. Thus, the progestin may be selected from progesterone, 17-hydroxyprogesterone, dihydroprogesterone, medroxyprogesterone acetate, norethindrone, norethindrone acetate, norethynodrel, ethynodioldiacetate, norgestrel, levo-norgestrel, gestodene, delta- 15-levonorgestrel, norgestimate, 17-deacetyl norgestimate, nomegesterol, nesterone, desogestrel and 3-keto-desogestrel. Preferred progestins are norethindrone acetate and 3-keto-desogestrel.

The selection of hormones most suited for transdermal delivery may be determined by conventional tests used in the art to determine skin permeability. The most common is the In Vitro Skin Permeation Chamber using hairless mouse skin or human cadaver skin. The literature contains much information on these tests and the following references are typical:

a) Kao J, Hall J. Skin Absorption and Cutaneous First Pass Metabolism of Topical Steroids: In Vitro Studies with Mouse Skin in Organ Culture. J Pharmacol Exp Ther 241(2), pp 482–487, 1987;

b) Tojo K, Lee C. A Method for Predicting Steady-state Rate of Skin Penetration In Vivo. J Invest Derm 92(1 ), pp 105–108, 1989;

c) Liu P, Higuchi WI, Song W, Kurihara-Bergstrom T, Good WR. Quantitative Evaluation of Ethanol Effects on Diffusion and Metabolism of β-Estradiol in Hairless Mouse Skin. Pharm Res 8(7), pp 865–872, 1991; and d) Roy S, Gutierrez M, Chiang C. Permeation of Norethindrone, Norethindrone Acetate and Norethindrone Diacetate Through Cadaver Skin. Pharm Res Suppl 6, p 1168, 1989.

In selecting suitable hormones, skin permeation and hence transdermal delivery rates are important, but also, the stability of the hormones in the formulation can be a factor. Stability can be assessed or measured in two basic ways: visual inspection and in vitro dissolution.

Visual inspection is generally conducted on both a macroscopic and a microscopic level for crystal formation. As for in vitro dissolution, there are tests for in vitro release rates which are standard in the art. Generally when these criteria are met, the transdermal delivery rates required are readily achieved.

The phases may comprise from one to four days, but these days need not be exactly twenty-four hour days. Obviously there are limits as to the flexibility available given that absence of hormone for too long would likely result in withdrawal bleeding, but for example, for a three day phase, the total number of hours might be 66 or 78, as opposed to 72. A preferred regimen uses phases comprising about three and about four days. Other combinations such as two and three or one and three, or three and three, or two and four, or one and four may be used.

Generally hormone replacement therapy is delivered without interruption. But, there may be instances where interruption could be desirable in which case, patches containing placebo or any other hormone-free agent may be included in a package. Examples of suitable alternative hormone-free agents include vitamins, such as iron supplements.

Generally, the quantities of estrogen and progestin incorporated in the formulation of the invention are dependent on the activity of the estrogen or progestin selected. In the present formulation, estrogen is administered continuously, in other words, it is always present in the formulation, while the progestin level is adjusted up or down to produce the required estrogen or progestin dominance. The selection of quantities is dependent on the type of estrogen or progestin since each hormone has its own specific activity.

Typically in the formulations described in U.S. Pat. No. 5,108,995, the amount of estrogen activity per unit dose may be equivalent in estrogenic activity to a range of from a minimum of about 0.3 mg of piperazine estrone sulphate to a maximum of about 2.5 mg of piperazine estrone sulphate. The amount of progestin activity per unit dose may be equivalent in progestagenic activity to a range of from a minimum of 0 mg to a maximum of about 5 mg of norethindrone.

Some preferred combinations include the following:

1. Three units doses of 0.75 mg piperazine estrone sulphate alternating with three unit doses of 0.75 mg of piperazine estrone sulphate with 0.35 mg of norethindrone.

2. Three unit doses of 0.75 mg piperazine estrone sulphate and 0.15 mg of norethindrone alternating with three unit doses of 0.75 mg of piperazine estrone sulphate and 0.35 mg of norethindrone.

Equivalent dosages for transdermal can be determined from hormone blood level measurements. Generally, it is thought that for the delivery rates contemplated for the patch formulations of the present invention, the amounts of hormones may be characterized as follows. Firstly, each phase would generally constitute a single patch, though a series of patches could be used to make up a phase. Patch size is dependent on, among other parameters, the length of the phase, and the potency of the hormone. For example, patches of 17-$\beta$ estradiol are currently available which provide transdermal delivery rates of about 50 $\mu$g/day. In such instance, the amount of 17-62 estradiol is 4 mg and the size of the patch is about 18 cm$^2$ with the actual reservoir being about 10 cm$^2$. In the case of a patch containing the two hormones, such as 17-$\beta$ estradiol and norethindrone acetate, the amounts of same would be 10 mg and 30 mg, respectively and the patch surface area would be 26 cm$^2$ to provide transdermal delivery rates of about 50 $\mu$g/day for 17-$\beta$ estradiol and about 250 $\mu$g/day for norethindrone acetate. 3-Keto-desogestrel is a more potent progestin and the amount incorporated in a patch might range from about 4 mg to about 30 mg to provide the required daily transdermal delivery rates. The range for 17-62 estradiol may be from about 1 mg to about 10 mg (in adhesive matrix reservoir, this could change in another type of patch), and for norethindrone acetate, the range may be from about 10 mg to about 100 mg.

The above combinations may also be grouped into three's and four's, starting with either three or four day groups and ending with the other.

There are a number of transdermal patches available commercially which may be used in the present method. Most important to remember is that the sequence of administration is critical to the present invention and the arrangement of the patches or their application in the predetermined order must be effected for the benefits of the invention to be obtained. Two such patches are described here for purposes of exemplification only, but others may be employed.

In one known system, a matrix of a solid adhesive of acrylic copolymer base containing hormones in dissolved form is employed. The system involves the use of a flexible backing foil which may comprise for example polyethylene terephthalate. A release liner forms another layer (in contact with the adhesive). A swellable polysaccharide, galactomannan is added to the adhesive matrix to improve the adhesion between the surface of the patch and hydrated skin, over the whole application, and to reduce irritation phenomena caused by occlusion effects. Preferably, a three layer laminate is produced of the backing foil, drug matrix and release liner. Currently, a commercial product of this nature is sold under the trade mark SYSTEN TTS.

Another commercial product is that available under the trade mark ESTRADERM. ESTRADERM TM is an estradiol transdermal system designed to release estradiol through a rate-limiting membrane continuously upon application to intact skin. The ESTRADERM TM system comprises five layers: a backing layer, a drug reservoir, a control membrane, an adhesive layer and a protective layer in that order from outside to inside. The qualitative composition of the ESTRADERM drug reservoir is estradiol, alcohol and hydroxypropyl cellulose.

For transdermal administration, as has already been stated, any suitable form of patch may be selected. Another which is known to be useful in the administration of hormone formulations is described in detail in U.S. Pat. No. 4,668,232 issued May 26, 1987 to Cordes and Wolff, the disclosure of which is incorporated herein by reference. In this U.S. patent, the system described is a four layer system comprising an impermeable backing or covering layer; a reservoir layer adjacent to the backing or covering layer; an adhesive layer permeable to the hormones and a protective layer which is removed before application of the patch. As described earlier, a three layer system may be used which comprises a backing layer, a drug matrix adhesive layer and a release liner.

An estrogen patch for the present invention may be prepared using an ethanolic gel type of drug reservoir. The weight of hormone, preferably 17-$\beta$ estradiol may comprise 4 mg. The patch may have a surface area of about 18 cm$^2$. In appearance it may be round with the reservoir comprising about 10 cm$^2$ of the patch. This generally provides a transdermal delivery rate of about 10 μg/day for 17-β estradiol. An estrogen/progestin patch may be prepared using an ethanolic gel type of drug reservoir with the amounts of hormones comprising 10 mg of 17-62 estradiol and 30 mg of norethindrone acetate, for example. The total contact area of such a patch would be about 20 cm² and have the appearance of eyeglasses with two joined reservoirs with each reservoir containing both drugs. This generally provides a transdermal delivery rate of about 50 μg/day of 17-β estradiol and about 250 μg/day of norethindrone acetate.

Typically, this preparation is for administration to post menopausal patients and/or those who are actively symptomatic.

The patches may be packaged, for example, in cartons containing a number of transdermal 17-β estradiol patches and a number of transdermal 17-β estradiol and norethindrone acetate patches. Each patch may be individually sealed in a protective pouch.

In this example a first 17-62 estradiol patch may be applied for the required number of days (although it is not essential to start with this phase), this patch is removed and one of the 17-β estradiol and norethindrone acetate patches is applied for the required number of days. The second patch is then removed and another 17-β estradiol patch is applied, and so on. The treatment is normally continued without interruption. The individual patches are usually changed every three or four days depending on the particular regimen, although the patches may be prepared for application for any combination of days within the one to four days limitation for the regimen.

Each new patch is applied to a different site. Preferred application sites are clean, dry and intact areas of skin, below the waistline on the trunk of the body. Preferably the buttock, hip or abdomen area is chosen since these areas of skin wrinkle least during body movement.

In the following examples, specific embodiments of the present invention are set forth. These are meant to be illustrative of the invention and are not meant to limit it in any way. All parts and percentages are by weight, unless indicated otherwise.

EXAMPLE 1

A three-day phase transdermal patch of 17-β estradiol (100 μg/day) is administered and alternated with a three-day phase transdermal patch of 17-β estradiol (100 μg/day) and norethindrone (0.35 mg/day). These patches are applied alternately and without interruption.

EXAMPLE 2

A three-day phase transdermal patch of 17-β estradiol (100 μg/day) is administered and alternated with a three-day phase transdermal patch of 17-β estradiol (100 μg/day) and norethindrone acetate (0.35 mg/day). These patches are applied alternately and without interruption.

EXAMPLE 3

A three-day phase transdermal patch of 17-β estradiol (50 μg/day) is administered and alternated with a three-day phase transdermal patch of 17-β estradiol (50 μg/day) and norethindrone acetate (0.15 mg/day). These patches are applied alternately and without interruption.

EXAMPLE 4

A three-day phase transdermal patch of 17-β estradiol (25 μg/day) is administered and alternated with a three-day phase transdermal patch of 17-β estradiol (25 μg/day) and norethindrone acetate (0.50 mg/day). These patches are applied alternately and without interruption.

EXAMPLE 5

An estrogen patch using an ethanolic gel type of drug reservoir incorporating about 4 mg. of 17-β estradiol is prepared having a surface area of about 18 cm². In appearance it is round with the reservoir comprising about 10 cm² of the patch. This generally provides a transdermal delivery rate of about 10 μg/day for 17-β estradiol.

An estrogen/progestin patch is prepared using an ethanolic gel type of drug reservoir with the amounts of hormones comprising 10 mg of 17-β estradiol and 30 mg of norethindrone acetate. The total contact area of such a patch is about 20 cm². The patches have the appearance of eyeglasses with two joined reservoirs with each reservoir containing both drugs. These patches generally provide a transdermal delivery rate of 50 μg/day of 17-β estradiol and 250 μg/day of norethindrone acetate.

The patches are packaged in cartons containing a number of transdermal 17-β estradiol patches and a number of transdermal 17-β estradiol and norethindrone acetate patches. Each patch is individually sealed in a protective pouch.

A first 17-β estradiol patch is applied for the required three days (although it is not essential to start with this phase), this patch is removed and one of the 17-β estradiol and norethindrone acetate patches is applied for four days. The second patch is then removed and another 17-β estradiol patch is applied, and so on. The treatment is continued without interruption. Each new patch is applied to a different site. Preferred application sites are clean, dry and intact areas of skin, below the waistline on the trunk of the body. Preferably the buttock, hip or abdomen area is chosen since these areas of skin wrinkle least during body movement.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material or composition of matter, process, process step or steps, or then present objective to the spirit of this invention without departing from its essential teachings.

I claim:

1. A method of treating a female in need of hormone replacement therapy comprising transdermally administering to said female a pharmaceutical patch regimen series consisting essentially of a series of transdermal patches arranged in alternating phases of dominant hormone activity of from about one day to about four days, said phases being selected from estrogen dominant activity phases and progestin dominant activity phases, each of said phases comprising at least one patch which is applied and removed in accordance with the particular dominant phase activity, said estrogen dominant activity phase consisting of administering a transdermal estrogen substance alone or administering a transdermal estrogen substance and a transdermal progestin substance, and said progestin dominant activity phase consisting of administering a transdermal progestin substance and a transdermal estrogen substance, the amount of progestin substance being alternately increased in the progestin dominant activity phase and decreased in the estrogen dominant activity phase to provide the required dominant activity.

2. A method as claimed in claim 1 wherein each phase is administered by a single patch.

3. A method as claimed in claim 1 wherein each phase is administered by a plurality of patches.

4. A method as claimed in claim 1 wherein the estrogen and progestin are selected from estrogens and progestins which provide levels of activity, equivalent to a transdermal delivery rate of from about 25 μg/day to about 100 μg/day of 17-β estradiol and from about 25 μg/day to about 1000 μg/day of norethindrone acetate or from about 5 μg/day to about 150 μg/day of 3-keto-desogestrel, with the proviso that the progestin is increased in the progestin dominant phase relative to the estrogen dominant phase to produce the required dominance.

5. A method as claimed in claim 1 wherein the estrogen dominant phase comprises an amount of 17-β estradiol sufficient to provide a transdermal delivery rate of from about 25 μg/day to about 100 μg/day and the progestin dominant phase comprises an amount of 17-62 estradiol sufficient to provide a transdermal delivery rate of from about 25 μg/day to about 100 μg/day and an amount of norethindrone acetate sufficient to provide a transdermal delivery rate of from about 25 μg/day to about 1000 μg/day.

6. A method as claimed in claim 5 wherein the estrogen dominant phase comprises about three days and the progestin dominant phase comprises about four days.

7. A method as claimed in claim 5 wherein the estrogen dominant phase comprises about four days and the progestin dominant phase comprises about three days.

8. A method as claimed in claim 5 wherein the amount of norethindrone acetate is sufficient to provide a transdermal delivery rate of from about 75 μg/day to about 500 μg/day.

9. A method as claimed in claim 5 wherein the amount of norethindrone acetate is sufficient to provide a transdermal delivery rate of from about 75 μg/day to about 300 μg/day.

10. A method as claimed in claim 1 wherein the estrogen dominant phase comprises an amount of 17-β estradiol sufficient to provide a transdermal delivery rate of from about 25 μg/day to about 100 μg/day and the progestin dominant phase comprises an amount of 17-β estradiol sufficient to provide a transdermal delivery rate of from about 25 μg/day to about 100 μg/day and an amount of 3-keto-desogestrel sufficient to provide a transdermal delivery rate of from about 5 μg/day to about 150 μg/day.

11. A method as claimed in claim 10 wherein the estrogen dominant phase comprises about three days and the progestin dominant phase comprises about four days.

12. A method as claimed in claim 10 wherein the estrogen dominant phase comprises the equivalent of about four days and the progestin dominant phase comprises about three days.

13. A method as claimed in claim 10 wherein the amount of 3-keto-desogestrel is sufficient to provide a transdermal delivery rate of from about 25 μg/day to about 150 μg/day.

14. A method as claimed in claim 1 wherein the estrogen dominant phase comprises an amount of 17-β estradiol sufficient to provide a transdermal delivery rate of about 50 μg/day and the progestin dominant phase comprises an amount of 17-β estradiol sufficient to provide a transdermal delivery rate of about 50 μg/day and an amount of norethindrone acetate sufficient to provide a transdermal delivery rate of about 300 μg/day.

15. A method as claimed in claim 14 wherein the estrogen dominant phase comprises about three days and the progestin dominant phase comprises about four days.

16. A method as claimed in claim 14 wherein the estrogen dominant phase comprises about four days and the progestin dominant phase comprises about three days.

17. A method as claimed in claim 1 wherein the estrogen dominant phase comprises an amount of 17-β estradiol sufficient to provide a transdermal delivery rate of about 50 μg/day and the progestin dominant phase comprises an amount of 17-β estradiol sufficient to provide a transdermal delivery rate of about 50 μg/day and an amount of norethindrone acetate sufficient to provide a transdermal delivery rate of about 150 μg/day.

18. A method as claimed in claim 17 wherein the estrogen dominant phase comprises about three days and the progestin dominant phase comprises about four days.

19. A method as claimed in claim 17 wherein the estrogen dominant phase comprises about four days and the progestin dominant phase comprises about three days.

20. A pharmaceutical package comprising a transdermal patch regimen for administration to a female in need of hormone replacement therapy wherein the package comprises a pharmaceutical patch regimen series consisting essentially of a series of transdermal patches arranged in alternating phases of dominant hormone activity of from about one day to about four days, each of said phases being selected from estrogen dominant activity phases and progestin dominant activity phases, each of said phases comprising at least one patch which is applied and removed in accordance with the particular dominant phase activity, said estrogen dominant activity phase consisting of a transdermal estrogen substance alone or a transdermal estrogen substance and a transdermal progestin substance, and said progestin dominant activity phase consisting of a transdermal progestin substance and a transdermal estrogen substance, the amount of progestin substance being alternately increased in the progestin dominant activity phase and decreased in the estrogen dominant activity phase to provide the required dominant activity.

21. A package as claimed in claim 20 wherein the estrogen and progestin are selected from estrogens provide levels of activity equivalent to a transdermal delivery rate of from about 25 μg/day to about 100 μg/day of 17-β estradiol and from about 25 μg/day to about 1000 μg/day of norethindrone acetate or from about 5 μg/day to about 150 μg/day of 3-keto-desogestrel, with the proviso that the progestin is increased in the progestin dominant phase relative to the estrogen dominant phase to produce the required dominance.

22. A package as claimed in claim 20 wherein the estrogen dominant phase comprises an amount of 17-β estradiol sufficient to provide a transdermal delivery rate of from about 25 μg/day to about 100 μg/day and the progestin dominant phase comprises an amount of 17-β estradiol sufficient to provide a transdermal delivery rate of from about 25 μg/day to about 100 μg/day and an amount of norethindrone acetate sufficient to provide a transdermal delivery rate of from about 25 μg/day to about 1000 μg/day.

23. A package as claimed in claim 22 wherein the estrogen dominant phase comprises about three days and the progestin dominant phase comprises about four days.

24. A package as claimed in claim 22, wherein the estrogen dominant phase comprises about four days and the progestin dominant phase comprises about three days.

25. A package as claimed in claim 22 wherein the amount of norethindrone acetate is sufficient to provide a transdermal delivery rate of from about 75 μg/day to about 500 μg/day.

26. A package as claimed in claim 22 wherein the amount of norethindrone acetate is sufficient to provide a transdermal delivery rate of from about 75 μg/day to about 300 μg/day.

27. A package as claimed in claim 20 wherein the estrogen dominant phase comprises an amount of 17-β estradiol sufficient to provide a transdermal delivery rate of from about 25 μg/day to about 100 μg/day and the progestin dominant phase comprises an amount of 17-β estradiol sufficient to provide a transdermal delivery rate of from about 25 μg/day to about 100 μg/day and an amount of 3-keto-desogestrel sufficient to provide a transdermal delivery rate of from about 5 μg/day to about 150 μg/day.

28. A package as claimed in claim 27 wherein the estrogen dominant phase comprises about three days and the progestin dominant phase comprises about four days.

29. A package as claimed in claim 27 wherein the estrogen dominant phase comprises the equivalent of about four days and the progestin dominant phase comprises the equivalent of about three days.

30. A package as claimed in claim 27 wherein the amount of 3-keto-desogestrel is sufficient to provide a transdermal delivery rate of from about 25 μg/day to about 150 μg/day.

31. A package as claimed in claim 20 wherein the estrogen dominant phase comprises an amount of 17-β estradiol sufficient to provide a transdermal delivery rate of about 50 μg/day and the progestin dominant phase comprises an amount of 17-β estradiol sufficient to provide a transdermal delivery rate of about 50 μg/day and an amount of norethindrone acetate sufficient to provide a transdermal delivery rate of about 300 μg/day.

32. A package as claimed in claim 31 wherein the estrogen dominant phase comprises about three days and the progestin dominant phase comprises about four days.

33. A package as claimed in claim 31 wherein the estrogen dominant phase comprises about four days and the progestin dominant phase comprises about three days.

34. A package as claimed in claim 20 wherein the estrogen dominant phase comprises an amount of 17-β estradiol sufficient to provide a transdermal delivery rate of about 50 μg/day and the progestin dominant phase comprises an amount of 17-β estradiol sufficient to provide a transdermal delivery rate of about 50 μg/day and an amount of norethindrone acetate sufficient to provide a transdermal delivery rate of about 150 μg/day.

35. A package as claimed in claim 34 wherein the estrogen dominant phase comprises about three days and the progestin dominant phase comprises about four days.

36. A package as claimed in claim 34 wherein the estrogen dominant phase comprises about four days and the progestin dominant phase comprises about three days.

37. A package as claimed in claim 20 wherein each phase comprises a single patch.

38. A package as claimed in claim 20 wherein each phase comprises a plurality of patches.

39. A pharmaceutical preparation for administration to a female in need of hormone replacement therapy comprising a patch regimen series consisting essentially of a series of transdermal patches arranged in alternating phases of dominant hormone activity of from about one day to about four days, each of said phases being selected from estrogen dominant activity phases and progestin dominant activity phases, each of said phases comprising at least one patch which is applied and removed in accordance with the particular dominant phase activity, said estrogen dominant activity phase consisting of a transdermal estrogen substance alone or a transdermal estrogen substance and a transdermal progestin substance, and said progestin dominant activity phase consisting of a transdermal progestin substance and a transdermal estrogen substance, the amount of progestin substance being alternately increased in the progestin dominant activity phase and decreased in the estrogen dominant activity phase to provide the required dominant activity.

* * * * *